United States Patent [19]

English

[11] 4,422,454
[45] Dec. 27, 1983

[54] EMERGENCY EXTRICATION APPLIANCE

[75] Inventor: Paul R. English, Charlotte, N.C.

[73] Assignee: Medical Specialties, Inc., Charlotte, N.C.

[21] Appl. No.: 385,501

[22] Filed: Jun. 7, 1982

[51] Int. Cl.³ .............................................. A61G 1/00
[52] U.S. Cl. ...................................... 128/134; 5/82 R
[58] Field of Search ............... 128/82, 83, 87 R, 87 C, 128/87 B, 89 R, 133, 134; 5/82 R, 82 B; 269/328, 322

[56] References Cited

U.S. PATENT DOCUMENTS

| | | | |
|---|---|---|---|
| 2,785,672 | 3/1957 | Napoli | 128/87 R |
| 3,315,671 | 4/1967 | Creelman | 128/134 |
| 3,469,268 | 9/1969 | Phillips | 5/82 |
| 3,620,211 | 11/1971 | Goodell et al. | 128/89 R |
| 3,724,453 | 4/1973 | Dixon et al. | 128/87 R |
| 4,024,861 | 5/1977 | Vincent | 128/87 R |
| 4,034,748 | 7/1977 | Winner | 128/87 R |
| 4,127,120 | 11/1978 | Applegate | 128/134 |
| 4,141,368 | 2/1979 | Meyer | 128/87 B |
| 4,143,654 | 3/1979 | Sherman | 128/87 R |
| 4,151,842 | 5/1979 | Miller | 128/87 R |
| 4,211,218 | 7/1980 | Kendrick | 128/87 R |
| 4,226,231 | 10/1980 | Andersen | 128/134 |
| 4,252,113 | 2/1981 | Scire | 128/134 |
| 4,267,830 | 5/1981 | Vick | 128/87 R |
| 4,299,209 | 11/1981 | Behrens et al. | 128/87 R |
| 4,299,211 | 11/1981 | Doynow | 128/89 R |

FOREIGN PATENT DOCUMENTS 650621 of 0000 U.S.S.R. .

*Primary Examiner*—John D. Yasko
*Attorney, Agent, or Firm*—Bell, Seltzer, Park & Gibson

[57] ABSTRACT

An emergency extrication appliance as disclosed, which is adapted for the extraction of an injured person from an automobile or other confined location. The appliance comprises a two part cervical collar which is adapted to encircle and immobilize the person's head and neck. Also, the appliance includes a relatively thin body support which includes a lower body portion adapted to encircle the lower back and chest, and a head support portion adapted to overlie the back of the neck and at least a portion of the head. A number of neck straps are mounted on the head support portion, with the straps including Velcro type fastening means for releasably interconnecting the same to the cervical collar and so as to substantially preclude relative movement therebetween. A single reinforcing stay extends vertically along the head support portion and lower body portion of the body support member, such that the appliance acts to effectively immobilize substantially the full length of the spine and the head of the wearer. The reinforcing stay terminates at a point spaced from the lower edge of the body support member, to define an inwardly flexible lower edge portion which is adapted to be curved inwardly to underlie the buttocks. Groin straps are mounted on the appliance and are adapted to extend across the flexible lower edge portion and through the crotch of the wearer, and so as to curve the lower edge portion to underlie the buttocks and thereby prevent slippage between the appliance and the wearer upon lifting of the appliance.

25 Claims, 16 Drawing Figures

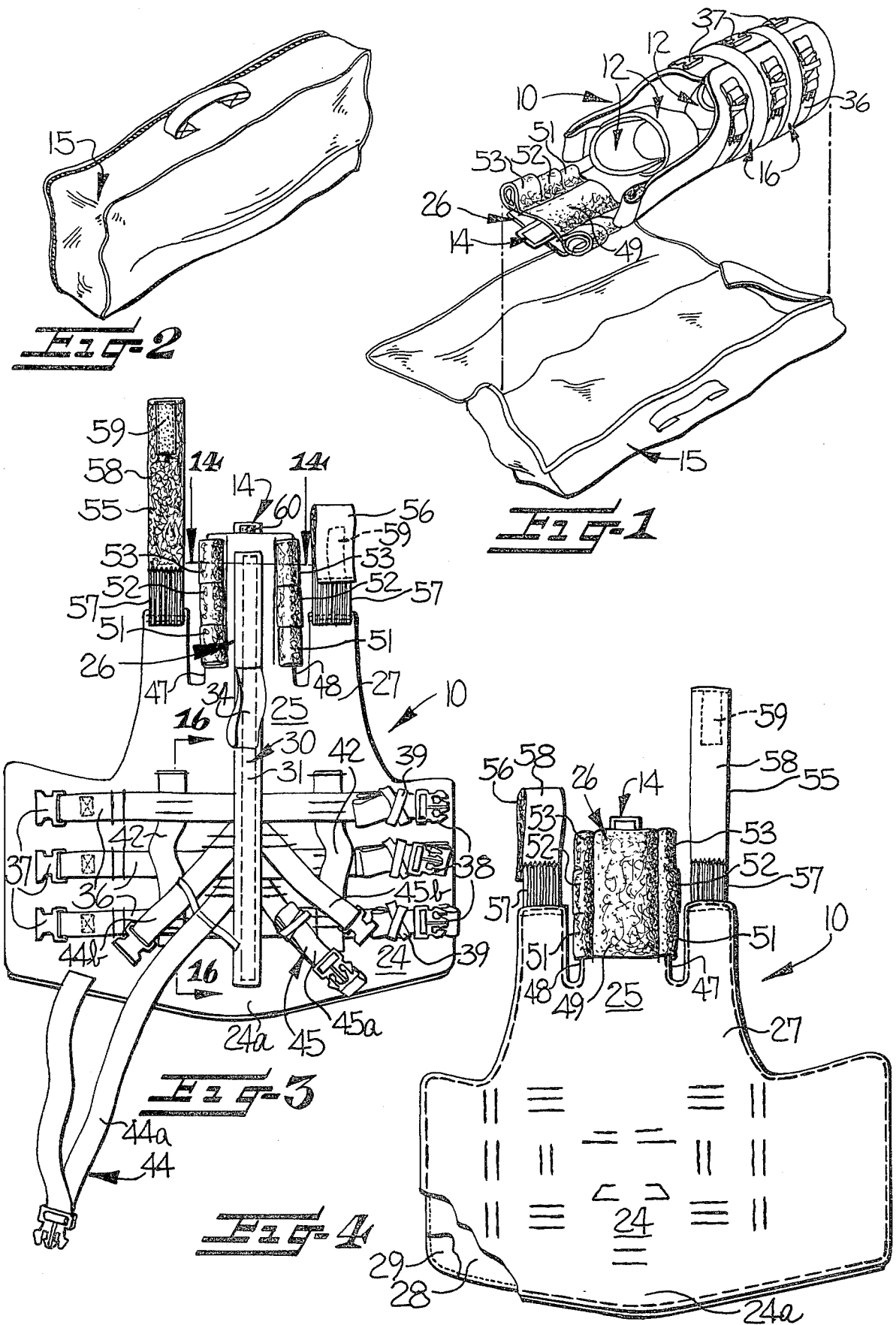

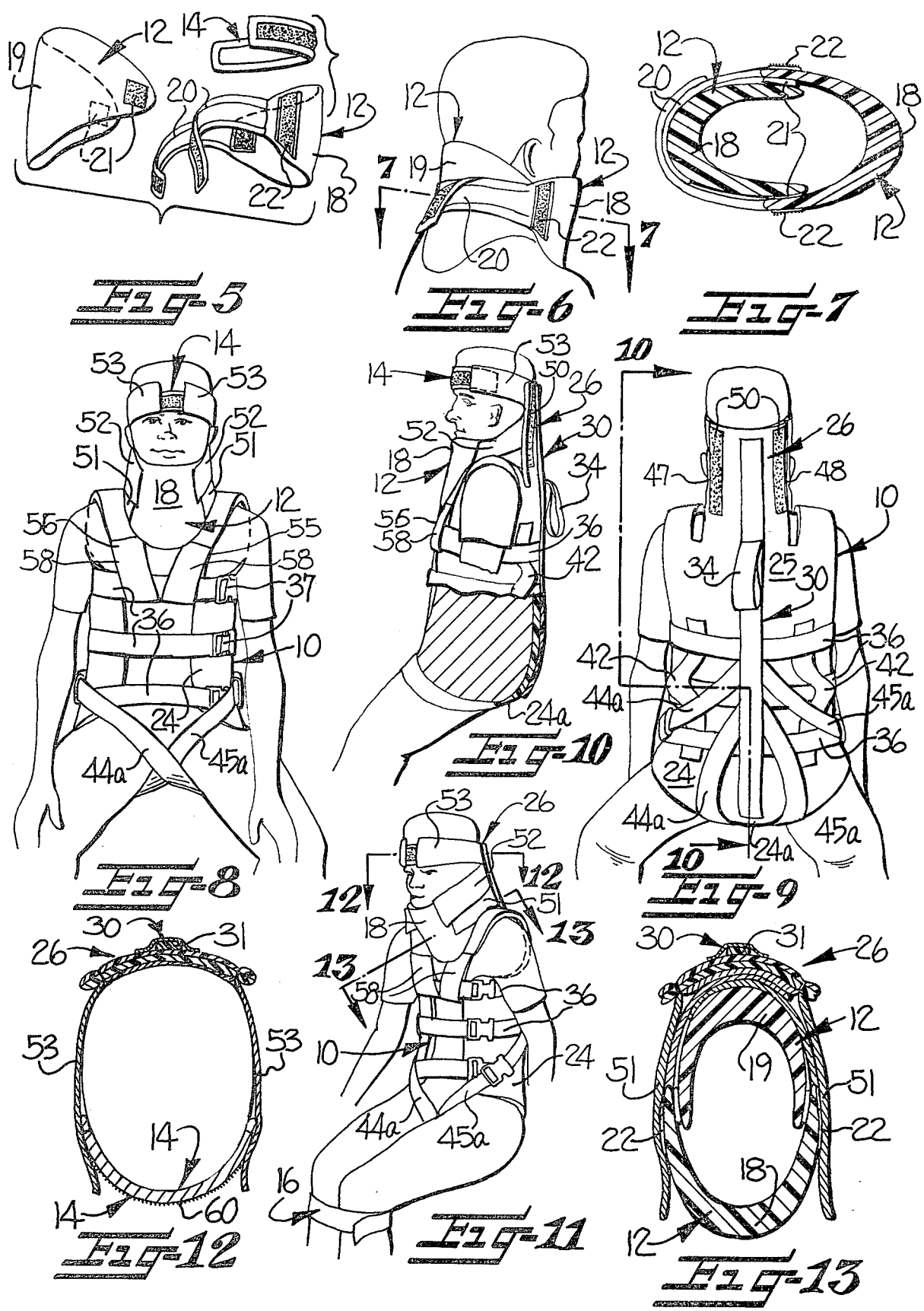

EMERGENCY EXTRICATION APPLIANCE

The present invention relates to an emergency extrication appliance for assisting in the extrication of an injured person from an automobile or other confined location, and where injury to the spine is suspected.

It has long been recognized that great care should be exercised when moving an injured person who has suffered a spinal injury, to assure that the spine is maintained as immobile as possible and thereby avoid further injury. Historically, immobilization was attempted by simply strapping the injured person to a rigid, flat wooden backboard. However, a backboard is not totally satisfactory since its size and width precludes its application in confined locations without substantial movement of the injured person, and it cannot conform to the shape of the body of the injured person. Thus, the person's body necessarily has to conform to the backboard, and further injury is thus possible.

More recently, extrication appliances of the type illustrated for example in U.S. Pat. No. 4,211,218 to Kendrick have been marketed, and which comprises a body member which is designed to wrap partially around the body of the injured person. Such appliances are sometimes sold with a one piece cervical collar which is adapted to encircle the injured person's neck. While such appliances represent a substantial improvement over the prior rigid backboard, it is not believed that they are able to fully conform to the injured person's body, it is not believed nor do they provide the desired degree of support along the full length of the person's spine.

It is accordingly an object of the present invention to provide an emergency extrication appliance which is able to closely conform to the contour of the person during its application, and which is able to effectively immobilize the full length of the injured person's spine, including the head and neck.

It is also an object of the present invention to provide an emergency extrication appliance which may be applied to the injured person in confined locations relatively easily and with minimum risk of further injury, and which may be utilized to transport the person while maintaining the full length of the spine effectively immobilized.

More particular objects of the present invention include the provision of an emergency extrication appliance of the described type which is substantially X-ray transparent, and which is able to securely support the injured person to permit the person to be lifted while in an upright position and without slippage of the appliance with respect to the person.

These and other objects and advantages of the present invention are achieved in the embodiment of the invention illustrated herein by the provision of an emergency extrication appliance which comprises a cervical collar adapted to encircle the wearer's neck to immobilize the head and neck, and a relatively thin, flexible body support which comprises a lower body portion which is adapted to encircle the lower back and chest of the wearer, an upper body portion adapted to overlie the upper back of the wearer, and a head support portion adapted to overlie the back of the neck and at least a portion of the head of the wearer. chest straps are provided for securing the lower body portion about the back and chest, andd neck straps are provided for releasably interconnecting the head support portion of the body and the cervical collar, so as to substantially preclude relative movement therebetween upon being interconnected.

In the preferred embodiment as specifically illustrated and described below, the cervical collar comprises a pair of U-shaped body members, each comprising a medial portion and opposite end portions. The body members are adapted to be positioned in a mating face to face arrangement encircling the neck of the wearer, with the medial portion of one of the members extending between the chin and sterum of the wearer and the medial portion of the other body member extending between the upper back and occipital region of the wearer. Also, Velcro type fastening means are provided for releasably securing the body members in such mating face to face arrangement.

The body support preferably is sized and shaped such that the lower body portion has a lengthwise dimension sufficient to extend to a point below the coccyx and so as to define a flexible lower edge portion which is adapted to overlie a substantial portion of the buttocks of the wearer. Groin straps are also provided which extend across the flexible lower edge portion and through the crotch of the wearer, and upon tightening, they act to curve the lower edge portion to underlie the buttocks. Thus when the body support is operatively positioned on a wearer in the seated or upright position, the curved lower edge portion supports the buttocks to prevent slippage between the appliance and the wearer upon the lifting of the appliance.

Some of the objects having been stated, other objects will appear as the description proceeds, when taken in connection with the accompanying drawings in which FIG. 1 is an exploded perspective view of an emergency extrication appliance in accordance with the present invention, together with a carrying case;

FIG. 2 is a perspective view of the emergency extrication appliance in its stowed configuration within its carrying case;

FIG. 3 is a rear elevation view illustrating the outside surface of the body support member of the emergency extrication appliance;

FIG. 4 is a front elevation view of the inside surface of the body support member;

FIG. 5 is a perspective view of the cervical collar and headband of the appliance;

FIG. 6 is a perspective view illustrating the cervical collar of FIG. 5 operatively positioned about a wearer's neck;

FIG. 7 is a sectional plan view of the collar taken substantially along the line 7—7 of the FIG. 6;

FIG. 8 is a front elevational view of the appliance of the present invention operatively positioned on a wearer;

FIG. 9 is a rear elevational view illustrating the appliance operatively positioned on a wearer;

FIG. 10 is a side elevational view, partly sectioned, of the operatively positioned appliance and taken substantially along the line 10—10 of FIG. 9;

FIG. 11 is a perspective view of the appliance operatively positioned on a wearer;

FIG. 12 is a sectional plan view taken substantially along the line 12—12 of the FIG. 11;

FIG. 13 is a sectional plan view taken substantially along the line 13—13 of FIG. 11;

Figure 14:
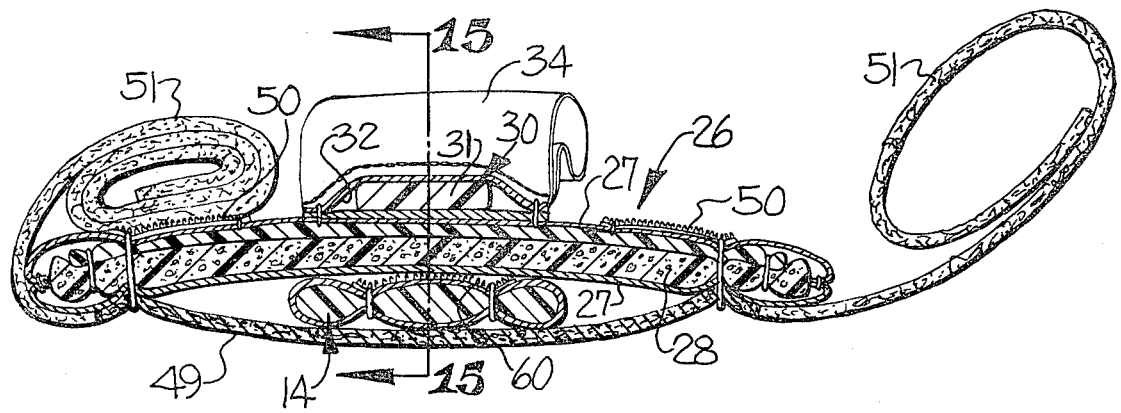
FIG. 14 is an enlarged sectional view of the head support portion of the appliance, and taken substantially along the line 14—14 of FIG. 3.

Referring more particularly to the drawings, there is illustrated a specific preferred embodiment of the invention which comprises a body support 10, a cervical collar 12, and a headband 14, all of which are adapted to be stowed in a carrying case 15 as seen in FIGS. 1 and 2. In the stowed configuration, the body support member 10 is rolled into a generally cylindrical configuration, and is held by two encircling retaining straps 16.

The cervical collar 12 is of the type specifically illustrated and described in the U.S. Patent to Gaylord 4,205,667, the disclosure of which is expressly incorporated herein. As best seen in FIGS. 5-7, the collar 12 comprises front and rear U-shaped body members 18 and 19 respectively, each comprising a medial portion and opposite end portions. The members 18 and 19 are adapted to be positioned in a mating face to face arrangement encircling the neck of the wearer with the oppositely directed end portions overlapping each other, and with the medial portion of the front body member extending between the chin and sternum of the wearer and the medial portion of the rear body member extending between the upper back and occipital region of the wearer. Each of the body members further comprises a core of relatively firm foam plastic material, and which has a exterior surface which generally conforms to a portion of a right cylindrical surface, and a fabric smoothly bonded to the core throughout the full area thereof.

The collar 12 further comprises means for releasably securing the two body members in their operative mating face to face arrangement. As illustrated, this fastening means comprises a flexible tab 20 mounted to each end portion of the front body member 18 and extending circumferentially therefrom. The inner surface of each tab 20 includes Velcro type hook means which is adapted to releasably engage the fabric cover of the rear body member 19. In addition, the rear member 19 mounts a fabric strip 21 on the exterior surface adjacent each of its end portions. The strips 21 are also covered with Velcro type hook means for engaging the fabric of front member 18. Thus two body members may be interconnected after being properly positioned about the neck of the wearer, by simply pressing the tabs 20 against the outer surface of the rear member 19, and subsequently disconnected by simply peeling the tabs 20 from the rear member, and the strips 21 from the front member 18. The front member of the collar further includes a fabric strip 22 secured along each side thereof, which also include Velcro type hook means for the purposes hereinafter described.

As best seen in FIGS. 3 and 4, the extrication appliance further includes a relatively thin, generally flexible body support 10 which defines an outside surface as seen in FIG. 3, and an inside surface as seen in FIG. 4. The body support 10 is composed of a lower body portion 24 having a widthwise dimension sufficient to substantially encircle the lower back and chest of the wearer, and a lengthwise dimension sufficient to extend to a point below the coccyx of the wearer and so as to define a lower edge portion 24a which is inwardly flexible and adapted to overlie the buttocks of the wearer in use, and as hereinafter further described. The body support 10 further includes an upper body portion 25 adapted to overlie the upper back of the wearer, and a head support portion 26 which extends lengthwise from the upper body portion on the side thereof opposite the lower body portion. The head support portion 26 is generally rectangular and has a length and width sufficient to overlie the back of the neck and at least a portion of the head of the wearer.

The body support 10 is also composed of a relatively thick layer 28 of plastic foam (note FIG. 15), and a relatively thin sheet 29 of solid plastic joined to the foam layer by stitching or the like. The foam layer 28 is preferably positioned adjacent the inside surface of the member to provide a cushioned surface against the body of the wearer, and the plastic sheet 29 is provided adjacent the outside surface to provide a desired degree of stiffness and strength to the member. Typically, the foam layer 28 has a thickness of about $\frac{3}{8}$ of an inch and comprises a nonabsorbent polyethylene foam having a density of about six pounds per cubic foot. The plastic sheet 29 typically comprises polyethylene having has a thickness of about 3/16 of an inch. A protective cover 27 of ballistic type nylon fabric encloses the foam layer and plastic sheet. As will be appreciated, these materials are substantially X-ray transparent, to permit the injured person to be X-rayed while confined in the appliance.

The body support 10 further includes a semi-rigid reinforcing member 30 mounted to extend lengthwise along substantially the full length of the outside surface of the body support, and at a medial location in the widthwise direction, note FIG. 3. The reinforcing member 30 is composed of a high density nylon stay 31 (note FIGS. 14 and 15), which is received within an elongate woven nylon fabric pocket 32 secured to the outside surface of the body support member. The pocket and stay terminate short of the lower edge portion 24a of the lower body portion by about three inches, and such that the lower edge portion is inwardly flexible and thereby adapted to curve inwardly to underlie the buttocks of the wearer.

Figure 15:
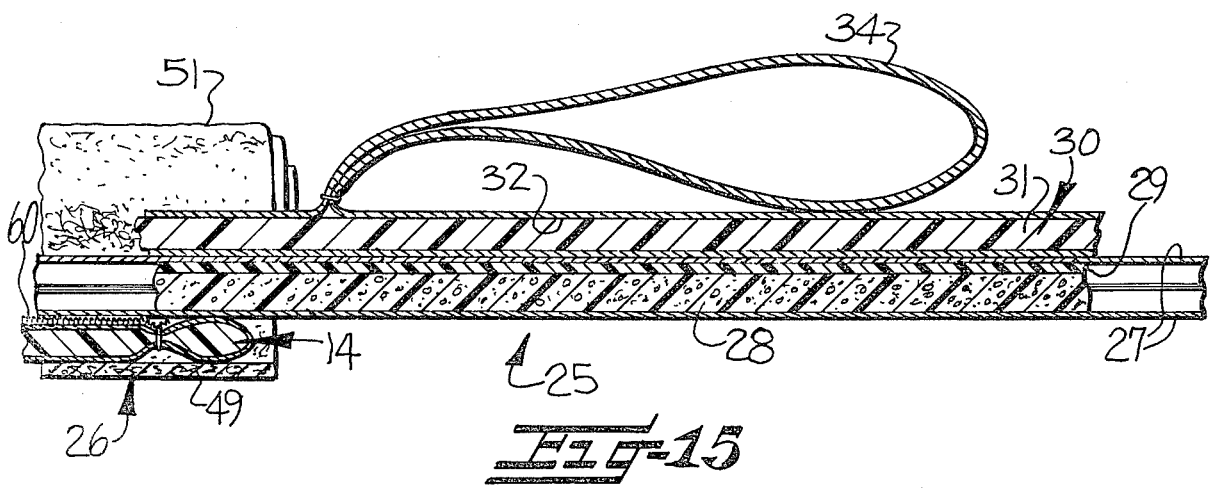
FIG. 15 is an enlarged sectional view of a medial portion of the body support member, and taken substantially along the line 15—15 of FIG. 14.
Figure 16:
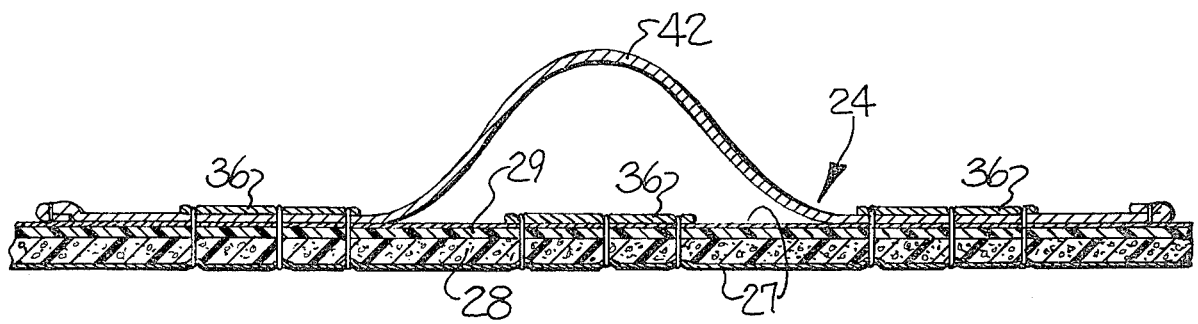
FIG. 16 is an enlarged sectional view of the handle strap of the appliance, and taken substantially along the line 16—16 of FIG. 3.

As best seen in FIGS. 3 and 15, a lifting loop 34 is formed in the pocket of the reinforcing member, so as to be positioned adjacent the upper body portion, and at the base of the head support portion. Thus the loop 34 is located centrally in the widthwise direction, and along the line of the reinforcing member 30.

Chest strap means are mounted to the body support for releasably securing the lower body portion in a generally cylindrical configuration encircling the lower back and chest of the wearer. In the illustrated embodiment, the chest strap means comprises three separate parallel straps 36 fixed on the outside surface of the member and extending in the widthwise direction. The straps 36, which typically comprise two inch woven nylon webbing of the type used in automobile seat belts, are secured to the body support member 10 by stitching or the like, and each strap mounts a buckle 37 and clasp 38 at their respective ends. The buckles and clasps are of known design, and permit the ends of the strap ends to be quickly connected and disconnected. A loop 39 is also secured to the body member adjacent the clasp end of each strap 36, for securing the strap in accordian fashion to thereby facilitate stowage.

Two parallel lifting straps 42 are secured to the outside surface of the lower body portion, and extend in the lengthwise direction, note FIG. 3. The medial portion of each lifting strap is gathered so as to be spaced from the body support, and such that it may be easily grasped by the hand of a rescuer in the manner described below.

Groin strap means are mounted to the outside surface of the body support member, for forming loops which extend through the crotch of the wearer. The groin strap means comprises a pair of flexible belts 44 and 45, which are similar in construction to the straps 36. Each of the belts 44, 45 is composed of first and second segments 44a, 44b and 45a, 45b respectively. The first segments 44a, 45a of each belt are disposed in a generally V-shaped orientation with the adjacent ends being secured to the outside surface along the line of the reinforcing member 30. The second segments 44b, 45b are disposed in a like orientation, with the adjacent ends being secured to a point spaced from the corresponding ends of the first segments in the lengthwise direction. The first segments 44a, 45a are each relatively long, and mount of a buckle at their free ends. The second segments 44b, 45b are relatively short, and mount a mating clasp at their free ends. Thus the segments 44a, 45b, are adapted to extend through the crotch of the wearer in a crossing arrangement as seen in FIG. 6 to releasably engage the clasp of the segment of the opposite belt. Alternatively, the segments 44a, 45a may be looped through the crotch to engine the corresponding belt segment. In either case, the segments 44a, 45a extend across the flexible lower edge portion 24a of the body support, and upon interconnection and tighening, they act to curve the lower edge portion to underlie the buttocks of the wearer in the manner best seen in FIG. 10.

The head support portion 26 of the body support member 10 defines two parallel side edges 47, 48, and a padded fabric cover 49 is provided which is secured to overlie the inside surface thereof. The outside surface of the head support portion mounts a fabric strip 50 along each side edge, which includes Velcro type hook means. The fabric cover 49 is of a widthwise length to extend laterally beyond each side edge, and the outer portions are divided to form three parallel adjacent straps 51, 52 and 53 which extend in the lengthwise direction from each side edge. As best seen in FIG. 3, the straps 51-53 may be rolled and secured to the adjacent strip 50 on the outside surface of the member for stowage purposes. Also, it will be noted in FIGS. 2 and 3, that the headband 14 may be also conveniently stored by placing it between the fabric cover 49 and the inside surface of the head support portion 26.

The appliance also includes a pair of shoulder straps 55, 56 extending lengthwise from the upper body portion 25, with one shoulder strap being disposed on each side of the head support portion. Each of the shoulder straps 55, 56 includes an elastic section 57, and an outer flexible fabric portion 58. The outer portion 58 mounts a strip 59 of Velcro type hook means adjacent its free end, and the fabric material of the portion 58 has a texture which is adapted to be releasably engaged by the hook means of the strip 59. Thus the outer portion of the strap may form a loop (note the strap 56 in FIGS. 3 and 4), with the strip 59 releasably engaging the fabric.

The headband 14 is sized to overlie the forehead of the wearer, and its outer surface includes a strip 60 of Velcro type hook means for the purposes described below.

The method of assembling the appliance to a seated person, such as would be the case with a person injured in an automobile accident, will now be described. Initially, the cervical collar 12 is applied to the person's neck, by placing the rear member 19 behind the neck and then placing the front member 18 across the front of the neck and in a mating face to face arrangement with the rear member. The two members are then interconnected by pressing the collar tabs 20 of the front member onto the fabric of the rear member. Upon completion, the collar provides firm support about the entire circumference of the wearer's head and neck, with the rear member also serving to fill the void at the rear of the wearer's neck.

Once the collar 12 is in position, the body support 10 is placed behind the injured person, with the inside surface being placed adjacent the person's back. The smooth nylon inside surface of the body support facilities this placement in confined locations. The chest straps 36 are then brought around the victim and interconnected, so that the lower body portion will substantially encircle the entirety of the lower back and chest of the wearer. Thus the buckles 37 of the chest straps will be prevented from directly contacting and penetrating into the chest of the wearer upon tightening of the straps. The belts 44, 45 are next either looped or crossed through the crotch, and then interconnected and tightened. The shoulder straps are then fastened by being drawn over the victim's shoulders, with the ends being looped under and over the top or center chest strap 36, and interconnected by joining the strip 59 to the fabric of the outer portion 58. The size of the victim will determine which chest strap is engaged.

As final steps, the head support portion 26 of the appliance is releasably interconnected to the cervical collar 12 in a manner which substantially precludes relative movement therebetween. For this purpose, the lower two straps 51, 52 on each side of the head support portion are placed over the Velcro strips 22 attached to the sides of the front member 18. After the collar is thus secured, the headband 14 is placed over the forehead, and the two uppermost straps 53 are secured thereto by interengagement eith the Velco strip 60. Thus the head becomes rigidly secured to the head support portion, with the rear collar member 19 serving to fill the void behind the wearer's neck, and the full length of the spine and the head are effectively immobilized.

To lift and transport the victim, the two retaining straps 16 supplied with the appliance are used to secure the victim's arms and/or legs, note FIG. 11. The two lifting straps 42 may then be grasped by the rescuer to lift the victim. Preferably, this is accomplished by one rescuer positioned on each side of the injured person, with each rescuer grasping a strap 42 with one hand and engaging the hand of the other rescuer behind the knees and under the thighs of the victim. Also, the lifting loop 34 may be used to facilitate positioning of the victim.

In the drawings and specification, there has been set forth a preferred embodiment of the invention, and although specific terms are employed, they are used in a generic and descriptive sense only and not for purposes of limitation. That which is claimed is:

1. An emergency extrication appliance for the extraction of an injured person from an automobile or other confined location and where injury to the spine is suspected, and with the appliance being characterized by the ability of closely conform to the contour of the person during its application, and once applied, by the ability to effectively immobilize the full length of the spine and the head, and comprising, a cervical collar adapted to encircle a wearer's neck to substantially immobilize the head and neck, a relatively thin, generally flexible body support comprising a lower body portion adapted to overlie the lower back of the wearer, and a head support portion having a length and width sufficient to overlie the back of the neck and at least a portion of the head of the wearer, an elongate semi-rapid reinforcing means mounted to said body support and extending medially along a lengthwise direction over at least a substantial portion of the length of said lower body portion and head support portion, to thereby overlie the spine of the wearer, chest strap means mounted to said body support for encircling the wearer's chest and releasably securing the lower body portion to the back of the wearer, and neck strap means for releasably interconnecting said head support portion of said body support and said cervical collar, and so as to substantially preclude relative movement therebetween upon being interconnected, whereby in its operative position on the wearer, the appliance acts to rigidify substantially the entire length of the spine and the head of the wearer.

2. An emergency extrication appliance for the extraction of an injured person from an automobile or other confined location and where injury to the spine is suspected, and with the appliance being characterized by the ability to closely conform to the contour of the person during its application, and once applied, by the ability to effectively immobilize the full length of the spine and the head, and comprising, a cervical collar adapted to encircle a wearer's neck to substantially immobilize the head and neck, a relatively thin, generally flexible body support comprising (a) a lower body portion having a widthwise dimension sufficient to substantially encircle the lower back and chest of the wearer, and having a lengthwise dimension sufficient to extend to a point below the coccyx and so as to define a lower edge portion which is adapted to overlie a substantial portion of the buttocks of the wearer, (b) an upper body portion adapted to overlie the upper back of the wearer, and (c) a head support portion extending lengthwise from said upper body portion on the side thereof opposite said lower body portion, with said head support portion having a length and width sufficient to overlie the back of the neck and at least a portion of the head of the wearer, chest strap means mounted to said body support for releasably securing the lower body portion in a generally cylindrical configuration encircling the lower back and chest of the wearer, groin strap means mounted to said lower body portion of said body support for forming a pair of releasable loops which are adapted to extend across said lower edge portion and through the crotch of the wearer and thereby curve the lower edge portion to underlie the buttocks of the wearer, and neck strap means for releasably interconnecting said head support portion of said body support and said cervical collar, and so as to substantially preclude relative movement therebetween upon being interconnected, whereby in its operative position on the wearer, the appliance acts to rigidify substantially the entire length of the spine and the head of the wearer.

3. The emergency extrication appliance as defined in claim 2 further comprising a pair of shoulder straps extending in a lengthwise direction from said upper body portion, with one shoulder strap disposed on each side of said head support portion, and with said shoulder straps having a length sufficient to be looped around and thus secured to said chest strap means.

4. The emergency extrication appliance as defined in either claim 2 or 3 further comprising head strap means mounted on said head support portion for releasably encircling the forehead of the wearer and so as to cooperate with said neck strap means to substantially preclude movement of the neck and head with respect to said head support portion.

5. The emergency extrication appliance as defined in either claim 2 or 3 further comprising elongate semi-rigid reinforcing means mounted along a lengthwise line extending substantially the full length of said body support at a medial location in the widthwise direction, to stiffen the body support against lateral flexure along such medial line.

6. The emergency extrication appliance as defined in claim 5 wherein the remaining portions of said body support member are free of any elongate reinforcing means, and whereby such remaining portions are relatively flexible.

7. The emergency extrication appliance as defined in either claim 2 or 3 wherein said body support is composed of a relatively thick layer of plastic foam, a relatively thin sheet of solid plastic secured to the foam layer, and a fabric cover enclosing the foam layer and plastic sheet.

8. The emergency extrication appliance as defined in either of claims 2 or 3 wherein said cervical collar comprises a pair of U-shaped body members which are adapted to be positioned in a mating face to face arrangement encircling the neck of the wearer, and fastening means for releasably securing said body members to each other in said mating arrangement.

9. The emergency extrication appliance as defined in claim 8 wherein each of body members of said cervical collar comprises an inner foam core and an outer fabric covering, with the exterior surface of each body member generally conforming to a portion of a right cylindrical surface, whereby said body members collectively define an exterior generally cylindrical surface when in said mating arrangement.

10. The emergency extrication appliance as defined in claim 9 wherein said neck strap means comprises at least one flexible neck strap extending in the widthwise direction from each side edge of said head support portion, and hook means mounted on one of said cervical collar and each of said neck straps for releasably engaging the other of said members.

11. An emergency extrication appliance for the extractin of an injured person from an automobile or other confined location and where injury to the spine is suspected, and with the appliance being characterized by the ability to closely conform to the contour of the person during its application, and once applied, by the ability to effectively immobilize the full length of the spine and the head, and comprising, a cervical collar adapted to encircle a wearer's neck to substantially immobilize the head and neck, a relatively thin, generally flexible body support defining an inside surface and an outside surface, and comprising
  (a) a lower body portion having a widthwise dimension sufficient to substantially encircle the lower back and chest of the wearer, and having a lengthwise dimension sufficient to extend to a point below the coccyx and so as to define a lower edge portion which is adapted to overlie a substantial portion of the buttocks of the wearer,
  (b) an upper body portion adapted to overlie the upper back of the wearer, and
  (c) a head support portion extending lengthwise from said upper body portion on the side thereof opposite said lower body portion, with said head support portion having a length and width sufficient to overlie the back of the neck and at least a portion of the head of the wearer,
semi-rigid reinforcing means mounted to extend lengthwise along substantially the full length of said body support member and at a medial location in the widthwise direction, said reinforcing means terminating short of said lower edge portion of said lower body portion and such that said lower edge portion is inwardly flexible and thereby adapted to curve inwardly to underlie the buttocks of the wearer,
chest strap means mounted to the outside surface of said body support for releasably securing the lower body portion in a generally cylindrical configuration encircling the lower back and chest of the wearer,
groin strap means mounted to the outside surface of said body support for forming at least one releasable loop which is adapted to extend across said flexible lower edge portion and through the crotch of the wearer and thereby curve the lower edge portion to underlie the buttocks of the wearer, and
neck strap means for releasably interconnecting said head support portion of said body support and said cervical collar,
whereby in its operative position on the wearer, the appliance acts to rigidify substantially the entire length of the spine and the head of the wearer, and the lower edge portion of said body support member is curved to underlie and support the buttocks to thereby prevent slippage between the appliance and the wearer upon lifting of the appliance.

12. The emergency extrication appliance as defined in claim 11 wherein said body support is composed of a relatively thick layer of plastic foam adjacent said inside surface thereof, a relatively thin sheet of solid plastic joined to the foam layer and adjacent said outside surface, and a fabric cover enclosing the two layers.

13. The emergency extrication appliance as defined in claim 12 wherein said plastic foam is about ⅜ inches thick and has a density of about six pounds per cubic foot, and said plastic sheet is about 3/16 inches thick.

14. The emergency extrication appliance as defined in claim 11 wherein said appliance further comprises a pair of shoulder straps extending lengthwise from said upper body portion, with one shoulder strap disposed on each side of said head support portion.

15. The emergency extrication appliance as defined in claim 14 wherein each of said shoulder straps includes an elastic segment, and fastening means for releasably securing the strap in the form of a loop, and such that each of the shoulder straps is adapted to be looped around and thus secured to said chest strap means.

16. The emergency extrication appliance as defined in claim 11 wherein said reinforcing means comprises an elongate pocket mounted to the outside surface of said body support member, and a stay received in said pocket.

17. The emergency extrication appliance as defined in claim 11 further comprising lifting loop means mounted to the outside surface of said body support and including a flexible loop secured along the medial line of said reinforcing means and adjacent said upper body portion.

18. The emergency extrication appliance as defined in claim 11 wherein said groin strap means comprises a pair of flexible belts, with each of the belts having first and second belt segments, and buckle means mounted to each of said belt segments for releasably interconnecting the same.

19. The emergency extrication appliance as defined in claim 18 wherein said two first belt segments are disposed in a generally V-shaped orientation which opens toward said lower edge portion, with the adjacent ends thereof being secured to said outside surface of said body support member at a central location in the widthwise direction, and said two second strap segments are disposed in a like orientation with the adjacent ends thereof being secured at a point spaced from the corresponding ends of the first belt segments in the lengthwise direction.

20. The emergency extrication appliance as defined in claim 11 wherein said appliance further comprises a band adapted to overlie the forehead of the wearer, and a flexible head strap extending in the widthwise direction from each side edge of said head support portion, and hook means mounted on one of said band and said head straps for releasably interconnecting the same.

21. An emergency extrication appliance for the extraction of an injured person from an automobile or other confined location and where injury to the spine is suspected, and with the appliance being characterized by the ability to closely conform to the contour of the person during its application, and once applied, by the ability to effectively immobilize the full length of the spine, and comprising,
  a cervical collar adapted to encircle a wearer's neck to substantially immobilize the same head and neck, said collar comprising
    (a) a pair of U-shaped body members each comprising a medial portion and opposite end portions, and which are adapted to be positioned in a mating face to face arrangement encircling the neck of the wearer with the oppositely directed end portions overlapping each other and with the medial portion of one of said body members extending between the chin and sternum of the wearer and the medial portion of the other body member extending between the upper back and occipital region of the wearer, each of said body members further comprising a core of relatively firm foam plastic material and which has an exterior surface which generally conforms to a portion of a right cylindrical surface, and a fabric smoothly bonded to said core throughout the full area thereof, and
    (b) fastening means for releasably securing said body members in said mating face to face arrangement, and a relatively thin, generally flexible body support comprising
  (a) a lower body portion having a widthwise dimension sufficient to substantially encircle the lower back and chest of the wearer, and having a lengthwise dimension sufficient to extend to a point below the coccyx, and so as to define a generally flexible lower edge portion which is adapted to overlie a substantial portion of the buttocks of the wearer,
  (b) an upper body portion adapted to overlie the upper back of the wearer, and
  (c) a head support portion extending lengthwise from said upper body portion on the side thereof opposite said lower body portion, with said head support portion having a length and width sufficient to overlie the back of the neck and at least a portion of the head of the wearer,
chest strap means mounted to said body support for releasably securing the lower body portion in a generally cylindrical configuration encircling the lower back and chest of the wearer,
groin strap means mounted to said body support member for forming at least one releasable loop which is adapted to extend across said flexible lower edge portion and through the crotch of the wearer and thereby curve the lower edge portion to underlie the buttocks of the wearer, and
neck strap means for releasably interconnecting said head support portion of said body support and said cervical collar, and so as to substantially preclude relative movement therebetween upon being interconnected,
whereby in its operative position on the wearer, the appliance acts to rigidify substantially the entire length of the spine and the head of the wearer, and the lower edge portion of said body support is curved to underlie and support the buttocks to thereby prevent slippage between the appliance and the wearer upon lifting of the appliance.

22. An emergency extrication appliance for the extraction of an injured person from an automobile or other confined location and where injury to the spine is suspected, and with the appliance being characterized by the ability to closely conform to the contour of the person during its application, comprising,
a relatively thin, flexible body support comprising
  (a) a lower body portion having a widthwise dimension sufficient to substantially encircle the lower back and chest of the wearer, and having a lengthwise dimension sufficient to extend to a point below the coccyx and so as to define a lower edge portion which is adapted to overlie a substantial portion of the buttocks of the wearer,
  (b) an upper body portion adapted to overlie the upper back of the wearer, and
  (c) a head support portion extending lengthwise from said upper body portion on the side thereof opposite said lower body portion, with said head support portion having a length and width sufficient to overlie the back of the neck and at least a portion of the head of the wearer,
semi-rigid reinforcing means mounted to extend lengthwise along substantially the full length of said body support and at a medial location in the widthwise dimension, said reinforcing means terminating short of said lower edge portion of said lower body portion and such that said lower edge portion is inwardly flexible and thereby adapted to curve inwardly to underlie the buttocks of the wearer,
chest strap means mounted to said body support member for releasably securing the lower body portion in a generally cylindrical configuration encircling the lower back and chest of the wearer,
groin strap means mounted to said body support member for forming at least one releasable loop which is adapted to extend across said flexible lower edge portion and through the crotch of the wearer and thereby curve the lower edge portion to underlie the buttocks of the wearer, and
head strap means extending in the widthwise direction from said head support portion of said body support for encircling the forehead of the wearer and thereby securing the wearer's head against said head support portion,
whereby in its operative position on the wearer, the appliance acts to rigidify substantially the entire length of the spine and the head of the wearer, and the lower edge portion of said body support is curved to underlie and support the buttocks to thereby prevent slippage between the appliance and the wearer upon lifting of the appliance.

23. The emergency extrication appliance as defined in claim 22 wherein said head strap means comprises a band adapted to overlie the forehead of the wearer, a flexible strap extending in the widthwise direction from each side edge of said head support portion, and interengagement means mounted to said band and each of said straps for releasably interconnecting the same.

24. The emergency extrication appliance as defined in claim 1 wherein the portions of said body member other than the portion upon which the reinforcing means is mounted, are free of any elongate reinforcing means, and whereby such other portions are relatively flexible.

25. The emergency extrication appliance as defined in claim 24 wherein said body support is composed of a relatively thick layer of plastic foam, a relatively thin sheet of solid plastic overlying the foam layer, and a fabric cover enclosing the foam layer and plastic sheet.

* * * * *

UNITED STATES PATENT AND TRADEMARK OFFICE
CERTIFICATE OF CORRECTION

PATENT NO. : 4,422,454
DATED : December 27, 1983
INVENTOR(S) : Paul R. English

It is certified that error appears in the above-identified patent and that said Letters Patent is hereby corrected as shown below:

```
Column 1, line 65 "chest" should be -- Chest --.

Column 1, line 67 "andd" should be -- and --.

Column 2, line 1, after "body" insert -- support --.

Column 2, line 11 "sterum" should be -- sternum -- .

Column 5, line 18, delete "of"

Column 5, line 25 "engine" should be -- engage --.

Column 6, line 39 "eith" should be -- with --.

Column 6, line 63 "of" (first occurence) should be -- to --.

Column 7, line 7 "rapid" should be -- rigid --.

Column 8, line 60 "tractin" should be -- traction --.
```

Signed and Sealed this

Tenth Day of April 1984

[SEAL]

Attest:

GERALD J. MOSSINGHOFF

Attesting Officer

Commissioner of Patents and Trademarks